United States Patent
Trogler et al.

(10) Patent No.: US 8,178,357 B2
(45) Date of Patent: May 15, 2012

(54) PEROXIDE CHEMICAL SENSOR AND SENSING METHOD

(75) Inventors: William C. Trogler, Del Mar, CA (US); Forest Bohrer, San Diego, CA (US); Andrew C. Kummel, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 29 days.

(21) Appl. No.: 12/668,953

(22) PCT Filed: Jul. 23, 2008

(86) PCT No.: PCT/US2008/008916
§ 371 (c)(1), (2), (4) Date: Jul. 6, 2010

(87) PCT Pub. No.: WO2009/017631
PCT Pub. Date: Feb. 5, 2009

(65) Prior Publication Data
US 2010/0297776 A1 Nov. 25, 2010

Related U.S. Application Data

(63) Continuation-in-part of application No. PCT/US2008/005743, filed on May 5, 2008.

(60) Provisional application No. 60/962,132, filed on Jul. 26, 2007.

(51) Int. Cl.
*G01N 27/04* (2006.01)
*G01N 27/00* (2006.01)

(52) U.S. Cl. .......... 436/135; 436/96; 436/149; 436/151; 436/181; 422/82.01; 422/82.02; 422/83; 422/88; 422/90; 422/98

(58) Field of Classification Search .................... 436/96, 436/127, 135, 149, 151, 181; 422/82.01, 422/82.02, 83, 88, 90, 98
See application file for complete search history.

(56) References Cited

U.S. PATENT DOCUMENTS 5,448,905 A 9/1995 Stetter et al.
(Continued)

FOREIGN PATENT DOCUMENTS

JP 08-304327 11/1996
(Continued)

OTHER PUBLICATIONS

Sergeyeva et al. Analytical Chimica Acta, vol. 391, 1999, pp. 289-297.*

(Continued)

*Primary Examiner* — Maureen Wallenhorst
(74) *Attorney, Agent, or Firm* — Greer, Burns & Crain Ltd.

(57) ABSTRACT

Sensors, sensing systems and sensing methods of the invention provide for detection of peroxides, including for example, vapor-phase $H_2O_2$ and organic peroxides such as di-tert-butyl peroxide. A sensor and sensing method of the invention uses at least two phthalocyanines, one of which exhibits an oxidation reaction with peroxides and the other of which exhibits a reduction reaction with peroxides. A peroxide is readily identified by a sensor of the invention when one of the at least two phthalocyanines exhibits increased resistance to current flow and the other of the at least two phthalocyanines exhibits decreased resistance to current flow.

15 Claims, 9 Drawing Sheets

U.S. PATENT DOCUMENTS

| | | | |
|---|---|---|---|
| 5,719,033 | A | 2/1998 | Ackley |
| 5,938,917 | A | 8/1999 | Mulchandani |
| 6,221,238 | B1 | 4/2001 | Grundig et al. |
| 6,433,356 | B1 | 8/2002 | Cahen et al. |
| 6,575,013 | B2 | 6/2003 | Bao et al. |
| 6,809,955 | B2 | 10/2004 | Bulovic et al. |
| 6,850,859 | B1 | 2/2005 | Schuh |
| 7,025,718 | B2 | 4/2006 | Williams |
| 2002/0167003 | A1 | 11/2002 | Campbell |
| 2005/0189240 | A1* | 9/2005 | Lin et al. ............ 205/782 |
| 2010/0176837 | A1* | 7/2010 | Kummel et al. .......... 324/765 |

FOREIGN PATENT DOCUMENTS

| | | |
|---|---|---|
| KR | 10-2000-0052860 | 8/2000 |
| KR | 10-2004-0062446 | 7/2004 |
| KR | 10-2004-0086196 | 10/2004 |
| WO | WO/2006/046798 | 5/2006 |

OTHER PUBLICATIONS

Qi et al. Electroanalysis, vol. 5, 1993, pp. 547-554.*

Zent et al. Planet Space Science, vol. 46, No. 6/7, 1998, pp. 795-803.*

Bohrer et al. Journal of the American Chemical Society, vol. 130, Mar. 6, 2008, pp. 3712-3713.*

Langley, Cathryn E., et. al., "Manganese Dixoide Graphite Composite Electrodes: Application to the Electroanalysis of Hydrogen Peroxide, Ascorbic Acid and NitriteStarch hydrolysis under low water conditions: A conceptual process design", *Analytical Sciences*, vol. 23, pp. 165-170 Feb. 10, 2007.

Bouvet, M., et. al., "Phthaiocyanine-based field-effect transistor as ozone sensor", *Sens. Actuators*, B 73, 63 (2001).

Bouvet, M., "Phthalocyanine-based field-effect transistors as gas sensors", *Anal. Bioanal. Chem.* 384, 366 (2006).

Chang, J.B., et. al., "Pu ntable polythiophene gas sensor array for low-cost electronic noses", *J. Appl. Phys.* 100, 014506 (2006).

Chang, J.B., et at "Effect of active layer thickness on bias stress effect in pentacene thin-film transistors", *Appl. Phys. Lett.* 88, 233513 (2006).

Chesterfield, R.J., et. al., "Variable temperature film and contact. resistance measurements on operating $n$-channel organic thin film transistors", *J. Appl. Phys.* 95, 6396 (2004).

Crone, B., et. al., "Electronic sensing of vapors with organic transistors", *Appl. Phys. Lett.* 78, 2229 (2001).

Goldmann, C., et, al, "Determination of the interface trap density of rubrene single-crystal field-effect transistors and comparison to the bulk trap density", *J. Appl. Phys.* 99, 034507 (2006).

Gomes, H.L., et. al., "Bias-induced threshold voltages shifts in thin-film.organic transistors", *Appl. Phys. Lett.* 84, 3184 (2004).

Gould, R.D., "Structure and electrical conduction properties of.phthalocyanine thin films", *Coord. Chem. Rev.*, 1996, 156, 237-274.

Guillaud, G. at al., "Metallophthalocyanines: Gas sensors, resistors and field effect transistors", *Coord. Chem. Rev.*; 1998, 178, 1433-1484.

Horowitz, G., et. al., "Temperature and gate voltage dependence of hole mobility in polycrystalline oligothiophene thin film transistors", *J. Appl. Phys.* 87, 4456 (2000).

Jung, S., et. al., "Temperature sensor using thermal transport properties in the subthreshold regime of an organic thin film transistor" *Appl. Phys. Lett.*, 90 062105 (2007).

Liao, F., et. al, "Organic TFTs as gas sensors for electronic nose applications", *Sens. Actuators.* B 107, 849 (2005).

Miller, C.W., at al., "Quantitative structural analysis of organic thin films: An x-ray diffraction study", *Phys. Rev. B* 72 104113 (2005).

Minari, T., et. al., "Temperature and electric-field dependence of the mobility of a single-grain pentacene field-effect transistor", *J. Appl. Phys.* 99 034506 (2006).

Pacheo-Londo, L., et, al,, "Review of the various analytical techniques and algorithms for detection and quantification of TATP", *Proc. SPIE*, 2005, 5778, 317-326.

Pannemann, Ch., et, al, "Nanometer scale organic thin film transistors with pentacene", *Microelectronic Engineering*, vol. 67-68 845-852, 2003.

Powell, M.J., et. al., "Time and temperature dependence of instability mechanisms in amorphous silicon thin-film transistors", *Appl. Phys. Lett.* 54, 1323 (1989).

Salleo, A., et. al., "Light-induced bias stress reversal in polyfluorene thin-film", *J. Appl. Phys.* 94, 471 (2003).

Someya, T. et.al., "Vapor sensing with α,ω-dihexyiquarterthiophene field-effect transistors: The role of grain boundaries", *Appl. Phys. Lett.* 81. 3079 (2002).

Schmechel, R., et. al., "Electronic traps in organic transport layers", *Phys. Status Solidi A* 201 , 1215 (2004)

Torsi, L. et. al., "Multi-parameter gas sensor based on organic thin-film-transistors", *Sens. Actuators*, B 67, 312, 2000.

Torsi, L. et. at, "Organic Thin-Film Transistors as Plastic Analytical Sensors", *Anal. Chem.* 77, 380A (2005).

Wang, L., et. al, "Nanoscale chemical sensor based on organic thin-film transistors", *Appl. Phys. Lett.* 85, 6386 (2004).

Wright, J.D., "Gas Adsorption on Phthalocyanines and its Effects on Electrical Properties" *Prog. Surf Sci.*, 1989, 31, 1-60.

Yang, R.D., et. al., "Ultrathin organic transistors for chemical sensing", *Appl. Phys. Lett.* (2007).

Zilker, S.J.. et. al., "Bias stress in organic thin-film transistors and logic gates", *Appl. Phys. Lett.* 79, 1124 (2001).

Zhou, R., et. al., "Phthalocyanines as Sensitive Matenais for Chemical Sensors", *Appl. Organomet. Chem.* 10, 557 (1996).

Zhu, Z.T., et. al., "Humidity sensors based on pentacene thin-film transistors" *Appl. Phys. Lett.* 81, 4643 (2002).

* cited by examiner

Metal-free Phthalocyanine

Metallophthalocyanine
(M=Fe, Co, Ni, Cu, Zn)

PEROXIDE CHEMICAL SENSOR AND SENSING METHOD

PRIORITY CLAIM AND REFERENCE TO RELATED APPLICATION

This application claims priority under pursuant to 35 U.S.C. §119 from prior provisional application Ser. No. 60/962,132 filed Jul. 26, 2007, and is a continuation-in-part that claims priority under 35 U.S.C. 120 from PCT/US2008/05743, which was filed on May 5, 2008.

STATEMENT OF GOVERNMENT INTEREST

This invention was made with government support under AFOSR Contract No. F49620-02-1-0288 and NSF Contract No. CHE-0350571. The government has certain rights in the invention.

FIELD

Fields of the invention include chemical sensing of peroxide-based vapors and chemresistors. The invention is particularly applicable to sensing of peroxide based residues, including residues of sterilization procedures and explosives, including, e.g., hydrogen peroxide, organic peroxides and other peroxide-based explosives. Chemical sensors of the invention have example applications in hospitals, laboratories, and military or industrial locations. Devices based upon sensors of the invention can be useful, for example, to detect gas leakages and sterilization residues, and as explosive vapor detectors and chemical warfare agent detectors.

BACKGROUND

Chemical sensing is a critical process in a large number of everyday household, manufacturing, health care, industrial, military, and scientific processes. A chemical sensor that can indicate the presence of a chemical of interest is useful to provide warnings, such as to indicate an unacceptable level of carbon monoxide or to provide a warning regarding the presence of an explosive vapor or a chemical warfare agent. Similarly, chemical sensors can provide information on the presence or absence of a particular chemical in a process control scheme. The presence or absence of a gas can provide feedback used to control a wide range of industrial processes. In the area of scientific research, many instruments including, for example, chromatography instruments benefit from sensitive chemical detectors.

Sensitivity is a critical aspect of chemical sensors. The more sensitive a sensor is, the lower level of chemical agent that it can detect. Accordingly, there is great interest in producing highly sensitive chemical sensors. Early warning regarding levels of sensed chemicals, faster control of processes responsive to particular levels of sensed chemicals, and better detection in difficult environments are achieved as sensitivity increases. Some particular example applications of interest in the art will now be discussed.

One application of interest is the detection of ultra-trace amounts of explosives and explosive-related analytes. Such detection is of critical importance in detecting explosives in a number of civilian and military or security applications, e.g., mine fields, military bases, remediation sites, and urban transportation areas. Low-cost and portability have clear additional advantages to such sensor applications.

In security applications, chemical sensors are preferable to other detection devices, such as metal detectors, because metal detectors frequently fail to detect explosives, such as those in the case of the plastic casing of modern land mines. Similarly, trained dogs can be both expensive and difficult to maintain in many desired applications. Other detection methods, such as gas chromatography coupled with a mass spectrometer, surface-enhanced Raman Spectroscopy, nuclear quadrupole resonance, energy-dispersive X-ray diffraction, neutron activation analysis and electron capture detection are highly selective, but are expensive and not easily adapted to a small, low-power package for broad distribution.

Vapor-phase detection of peroxides is critically important for many health care, military and industrial safety applications. Hydrogen peroxide ($H_2O_2$) is a common oxidant, used industrially for paper bleaching and specialty chemical manufacture. It is also used in medical facilities as a chemical disinfectant. $H_2O_2$ is quite toxic; in the vapor phase 75 ppm (which may be present from the vapor of 30% $H_2O_2$ in water), is immediately hazardous to health, and the OSHA permissible exposure limit (PEL) for an 8 hour period is 1 ppm. Even those levels can be unsuitable for hospitalized patients, and $H_2O_2$ is an important sterilization tool for many hospital applications, such as surgical instrument sterilization, drug container sterilization, and room sterilization. Other techniques are unsatisfactory from a sterilization perspective, but use of $H_2O_2$ creates a risk of residues that are harmful at OSHA or even lower levels. Due to its widespread use and toxicity, vapor-phase monitoring of hydrogen peroxide is a necessity.

Concentrated hydrogen peroxide solutions are also precursor materials for organic peroxide based explosives, which are commonly used by terrorists in improvised explosive devices, making detection of both organic peroxides and hydrogen peroxide important to military and law-enforcement agencies.

Peroxide-based explosives, such as triacetone triperoxide (TATP), have seen marked increase in use over the past ten years. TATP in particular has been implicated in the London bombings of Jul. 7, 2005, as well as in the attempted airplane bombing by Richard Reid in December 2001. It has been widely used in improvised explosive devices by terrorists in countries (e.g. Israel) where the sale of high explosives is carefully monitored. TATP is a volatile compound (vapor pressure $5.2*10^{-2}$ Torr under ambient conditions) susceptible to detonation from heat, friction and shock, and it is primarily used in illegal activities rather than for military applications.

There are a variety of detection methods currently being developed and used for the detection of hydrogen peroxide and organic peroxides. These technologies include chromatographic/spectroscopic platforms, mass spectrometric systems, amperometric sensors, and fluorescent chemical assays. The chromatographic systems include gas chromatography and liquid chromatography (LC and HPLC) interfaced with FTIR and fluorescence detection. These systems offer high sensitivity and selectivity, but suffer from such drawbacks as relative size and lack of portability, high power demands, and sophisticated computational requirements. Mass spectrometry is widely used and suffers from similar drawbacks. Amperometric sensors and fluorescent chemical assays are extremely sensitive, and can be used to detect trace amounts of peroxides, but these methods only detect liquid/solid peroxides and may be susceptible to false positives.

Cross-reactive sensor array reactive sensor arrays have been shown to discriminate between chemicals in complex mixtures, and under favorable conditions can be used for field detection to identify compounds of interest in a complex background. See, Albert et al., "Cross-reactive Chemical Sensor Arrays", Chem. Rev. 2000, 100, 2595-2626. Metallophthalocyanines (MPcs) are compounds that have been used in chemiresistive sensors. See, Gould, R. D. Structure and Electrical Conduction Properties of Phthalocyanine Thin Films, Coord. Chem. Rev. 1996, 156, 237-274. The responses of MPc films to various oxidizing gases at constant direct current (DC) bias has been studied, resulting in a large body of literature on the influence of $O_2$, $NO_2$, $O_3$, and $H_2O$ analytes on MPc resistive sensors. See, Snow, A. W. et al., "Phthalocyanine Films in Chemical Sensors;" *Phthalocyanines: Properties and Applications*; Lever, A. B. P., Ed; John Wiley and Sons: New York, 1989; Vol. 1, p. 341; Wright, J. D., et al, Gas Adsorption on Phthalocyanines and its Effects on Electrical Properties, Prog. Surf. Sci. 1989, 31, 1-60.

Metallophthalocyanines are readily prepared in a simple, one-pot synthesis of the appropriately substituted phthalonitrile and metal salt of interest by refluxing in a high-boiling alcohol with a catalytic amount of strong base for several hours Metallophthalocyanines have been synthesized with nearly every metal in the periodic table. The phthalocyanines studied most are those of the late first row transition metals, such as iron, cobalt, nickel, copper, and zinc. Phthalocyanines are generally p-type semiconductors, with holes being the active charge carriers. N-type metallophthalocyanines semiconductors are also known. Perfluorinated metallophthalocyanines, where the 16 outer protons are replaced by fluorine atoms are n-type semiconductors. Metallophthalocyanines films have been shown to exhibit ohmic conductivity and space charge limited conductivity.

Conductivity in phthalocyanines films is influenced strongly by atmospheric "dopants," primarily $O_2$. When phthalocyanines thin films are exposed to $O_2$, the films become doped and the conductivity increases dramatically. This air-induced conductivity has been attributed to different mechanisms. Resistive sensing studies with p-type phthalocyanines thin films have focused primarily on their interaction with oxidizing gases, such as ozone and $NO_x$. See, e.g., Lee, Y. L. et al, "Effects of Substrate Temperature on the Film Characteristics and Gas-Sensing Properties of Copper Phthalocyanine Films, Appl. Surf. Sci. 2001, 172, 191-199; Liu, C. J et al., Response Characteristics of Lead Phthalocyanine Gas Sensor: Effect of Operating Temperature and Postdeposition Annealing, Journal of Vacuum Science & Technology A-Vacuum Surfaces and Films, 1996, 14(3), 753-756; Sadaoka, Y, et al., "Fast $NO_2$ Detection at Room Temperature with Optimized Lead Phthlocyanine Thin-Film Structures", Sens. Actuators, B 1990, 148-153. Phthalocyanines films are easily oxidized by $NO_x$, forming charge transfer complexes, which inject holes and increase film currents. The interaction of phthalocyanines films with reducing gases, such as $NH_3$, has the opposite effect. Decreased current upon analyte binding to these films has been attributed to electron donation from the reducing gas to trap charge carriers. Bohrer, F. I. et al, Gas Sesning Mechanism in Chemresitive Cobalt and Metal-Free Phthalocyanine Thin Films", J. Am. Chem. Soc. 2007, 129, 5640-5646.

$H_2O_2$ interactions with CoPc have been extensively studied in solution phase amperometric apparatuses. It has been reported that FePc and CoPc can electrochemically catalyze both oxidation and reduction of $H_2O_2$. Electrooxidation of $H_2O_2$ has been found to occur over electron-deficient films, which agrees with the use of hole-conducting, $O_2$ doped FePc and CoPc films in the present invention. From the drastic current loss upon exposure of FePc and CoPc to $H_2O_2$ it is apparent that chemisorption and subsequent oxidation of $H_2O_2$ (and concurrent reduction of the MPc film) is occurring. The irreversibility of the current reduction in the FePc films suggests that some further reaction within the film is occurring, such as the formation of the μ-oxo dimer of FePc. The mechanism of interaction of $H_2O_2$ with CuPc and $H_2$Pc is quite different. These films are oxidized by the dosing of $H_2O_2$' which may arise from homolytic cleavage of $H_2O_2$ to hydroxyl radicals, and electron extraction from the organic ring of the phthalocyanine.

The interaction of di-tert-butyl peroxide with MPc films has not been reported in the literature. $H_2$Pc and CoPc show minimal responses when dosed with di-tert-butyl peroxide, suggesting that simple physisorption is occurring, rather than redox chemistry. In contrast, CuPc is oxidized by di-tert-butyl peroxide, likely by a similar mechanism to $H_2O_2$: homolytic cleavage of the peroxide bond followed by electron extraction from the organic ligand. FePc is strongly oxidized by di-tert-butyl peroxide in a similar mechanism to that of CuPc.

In contrast to the redox reactions explained above, the interactions of phthalocyanines with common interferent vapors such as water, volatile organic compounds (VOCs), or other electron donors, involve coordination of the molecules to the metallophthalocyanine metal center and hole destruction in the semiconductor film by oxygen displacement, as well as hole trapping by electron donor ligands. Analytes bind to open surface metal coordination sites and compete with $O_2$ for occupied metal surface sites. There is the additional possibility of weak binding (physisorption) to the organic region of the phthalocyanines molecule for noncoordinating analytes, which may be governed by weak hydrophobic and possibly charge transfer interactions. Metal-analyte coordination strength has been shown to govern analyte binding and therefore the response of CoPc chemiresistive sensors to non-oxidizing vapors. Similarly, for $H_2$Pc chemiresistive sensors, the hydrogen bonding of analyte to the two interior NH protons has been found to primarily govern sensor responses to water and volatile organic compounds.

SUMMARY OF THE INVENTION

Figure 1:
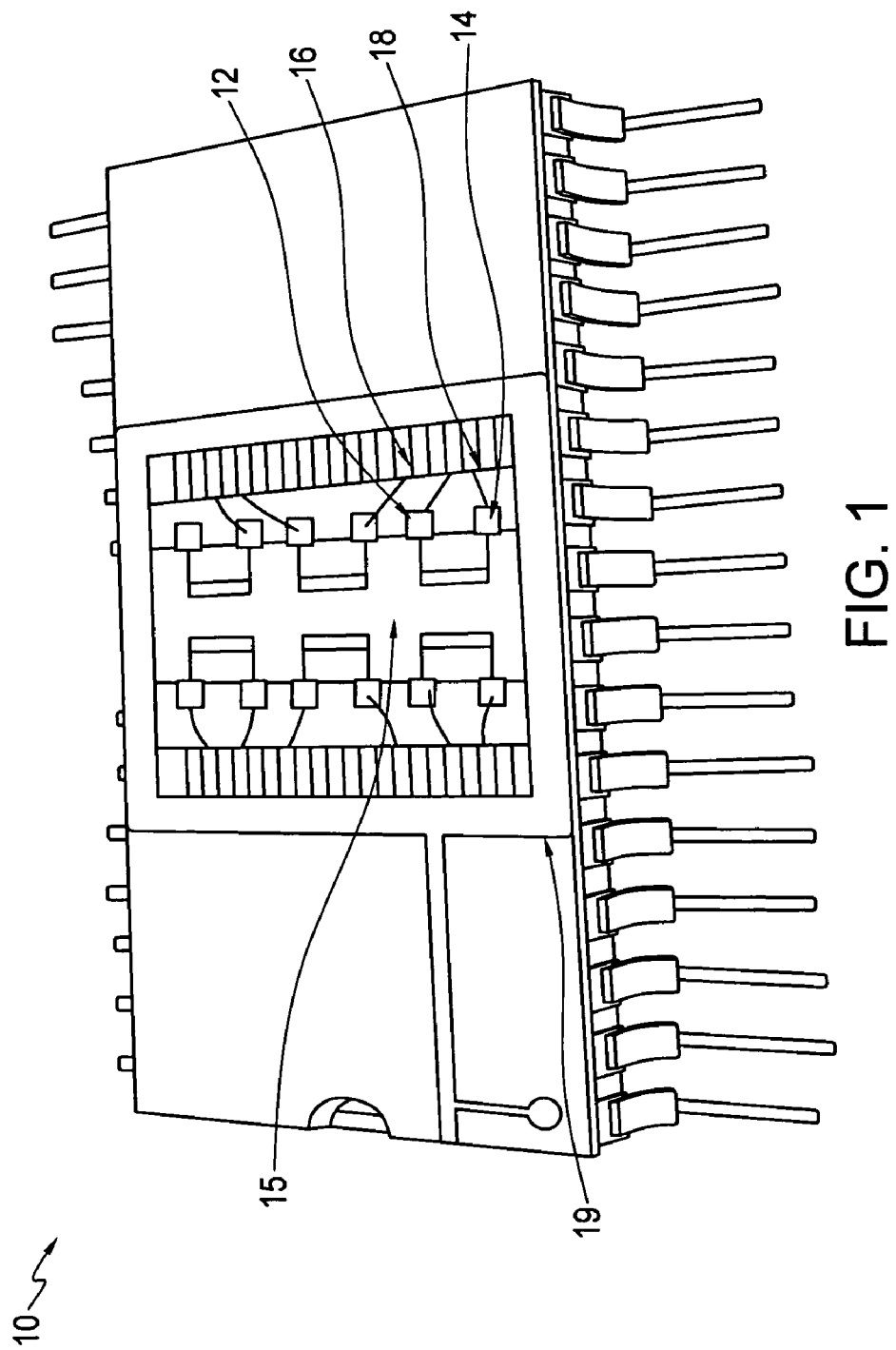
FIG. 1 illustrates a preferred embodiment peroxide sensor of the invention.

Sensors, sensing systems and sensing methods of the invention provide for detection of peroxides, including for example, vapor-phase $H_2O_2$ and organic peroxides such as di-tert-butyl peroxide. A sensor and sensing method of the invention uses at least two phthalocyanines, one of which exhibits an oxidation reaction with peroxides and the other of which exhibits a reduction reaction with peroxides. A peroxide is readily identified by a sensor of the invention when one of the at least two phthalocyanines exhibits increased resistance to current flow and the other of the at least two phthalocyanines exhibits decreased resistance to current flow.

DETAILED DESCRIPTION OF THE PREFERRED EMBODIMENTS

Embodiments of the invention provide sensors and methods that can quickly distinguish peroxides from other oxidizing agents. Sensors and sensing methods of the invention provide for detection of peroxides, including for example, vapor-phase $H_2O_2$ and organic peroxides such as di-tent-butyl peroxide. A sensor and sensing method of the invention uses at least two phthalocyanines, one of which exhibits an oxidation reaction with peroxides and the other of which exhibits a reduction reaction with peroxides. A peroxide is readily identified by a sensor of the invention when one of the at least two phthalocyanines exhibits increased resistance to current flow and the other of the at least two phthalocyanines exhibits decreased resistance to current flow.

Sensors and sensing methods are generally applicable to peroxides and can detect various peroxides of interest to general safety and security applications. Additional example peroxides that can be detected include volatile peroxide-based explosives such as triacetone triperoxide (TATP) and hexamethylene triperoxide diamine (HMTD).

A preferred embodiment of the invention is a sensing system for sensing vapor phase peroxides. The preferred sensing system includes a pulsed, dosing apparatus that provides analyte doses to at least two phthalocyanine chemiresistors, one of which exhibits reduced current after reacting with peroxides and the other increased current. The system monitors the resistance of each of the chemresistors, and determines the presence of peroxides when the two conditions are met. The amount of resistance increase in one of the chemresistors and the amount of resistance decrease in the other of the chemresistors can quantify the peroxides sensed, as well.

Sensors, sensing methods and sensing systems of the invention can use metal phthalocyanines. Example metal phthalocyanines that can be used in the invention include iron phthalocyanines, cobalt phthalocyanines, copper phthalocyanines, and metal-free phthalocyanine. Sensors, sensing methods and sensing systems of the invention can also use metal-free phthalocyanines. Other phthalocyanines include metallophthalocyanines, such as zinc and nickel phthalocyanines, which exhibit similar behavior to copper phthalocyanine. Chemically modified phthalocyanines can also be used.

Example materials include copper phthalocyanine (CuPc), $CuC_{32}N_8H_{16}$, cobalt phthalocyanine (CoPc), $CoC_{32}N_8H_{16}$, metal-free phthalocyanine ($H_2Pc$), $C_{32}N_8H_{18}$, Copper-hexadecafluorophthalocyanine ($F_{16}CuPc$)($F_{16}CuC_{32}N_8H_{16}$).

Preferred embodiments of the invention include chemresistors based upon thin phthalocyanine films, e.g., ~1000 nm or less. In a preferred embodiment, a phthalocyanine film that oxidizes in response to peroxides is deposited over first set of electrode fingers and another phthalocyanine film that reduces is deposited over a second set of electrode fingers. The resistance of the two films is monitored through the electrodes.

Other preferred embodiments of the invention include organic ultra-thin (one or a few monolayers) phthalocyanine film transistor chemresitors, one with a reduction response to peroxides and one with an oxidation response to peroxides. Preferred embodiments of the invention make use of ultra thin film transistor chemresistors with nearly monolayer thin film channels that act as super-sensitive detectors of trace levels of peroxides.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIG. 1 shows an example embodiment phthalocyanine chemresistor peroxide sensor 10 of the invention. The sensor 10 includes a first phthalocyanine region 12 exhibits decreased resistance when exposed to peroxides and a second region 14 that exhibits increased resistance when exposed to peroxides. Electrodes 16, 18 permit the resistance of the regions 12, 14 to be measured. A peroxide is unambiguously detected when the region 12 exhibits decreased resistance and the region 14 exhibits increased resistance. The regions 12, 14 are formed on a substrate 15.

The FIG. 1 sensor 10 is readily fabricated by the deposition of thin films (e.g., ~10-1000 and preferably ~10-100 nm) of phthalocyanines on interdigitated electrodes 16, 18. A wire bonding package 19 permits connection to outside circuits in the example package. An example spacing of the electrode fingers is ~5 μm. In this embodiment, separate semiconducting layers of phthalocyanines having different reactions to peroxides are placed between sets of narrowly spaced electrodes 16, 18 and a reasonable current can be measured from each. The phthalocyanines films can be deposited by epitaxial growth via vacuum deposition, allowing precise control of the growth conditions, film thickness, and film morphology.

In example experimental embodiments, interdigitated electrodes were prepared by standard photolithography and lift-off processing on thermally grown $SiO_2$ (thickness of 1 μm) on (100) Si substrates. The electrodes consisted of 45 pairs of gold fingers, spaced 5 μm apart, with an electrode width of 2 mm. An adhesion layer of 5 nm Ti was applied first, followed by 45 nm of Au for a total electrode thickness of 50 nm. Six pairs of electrodes were grown on each substrate to verify sensor reproducibility and increase yield.

Figure 2:
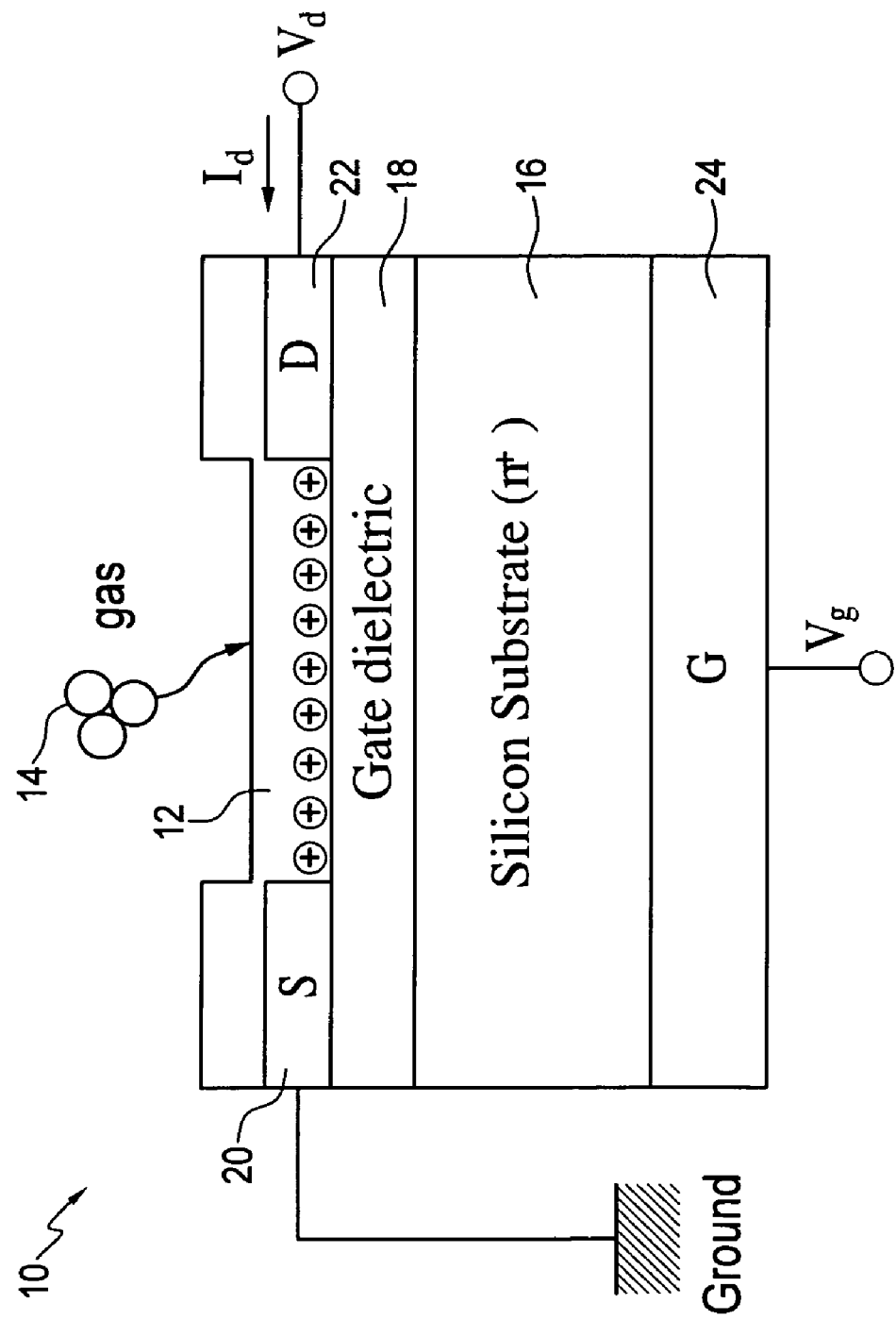
FIG. 2 illustrates another preferred embodiment peroxide sensor of the invention.

The regions 12, 14 can take many forms as thin or ultra-thin (approximately >10 nm) films, and the regions of phthalocyanines films can be replicated in arrays. While a simple chemrsistor is illustrated in FIG. 1, other configurations that permit the measurement of the resistance of two separate phthalocyanine regions having different peroxide responses can be used in accordance with other embodiments of the invention. As one example, FIG. 2 shows a thin film transistor 20 that has a phthalocyanine thin film channel 12. The FIG. 2 embodiment is formed on a silicon substrate 15. While the example embodiment is a silicon based device, other material systems can also be used. Gate dielectric 22, e.g., silicon dioxide, isolates source 24 and drain 26 electrodes, and a gate electrode 28 is formed on an opposite side of the substrate 15.

An additional transistor with a different phthalocyanine channel having an opposite peroxide reaction provides a peroxide sensor according to the invention. Fabrication and additional details of the thin film transistor 20 are described in PCT/US08/05743, filed May 5, 2008 and entitled ULTRATHIN ORGANIC TFT CHEMICAL SENSOR, MAKING THEREOF, AND SENSING METHOD.

Figure 3:
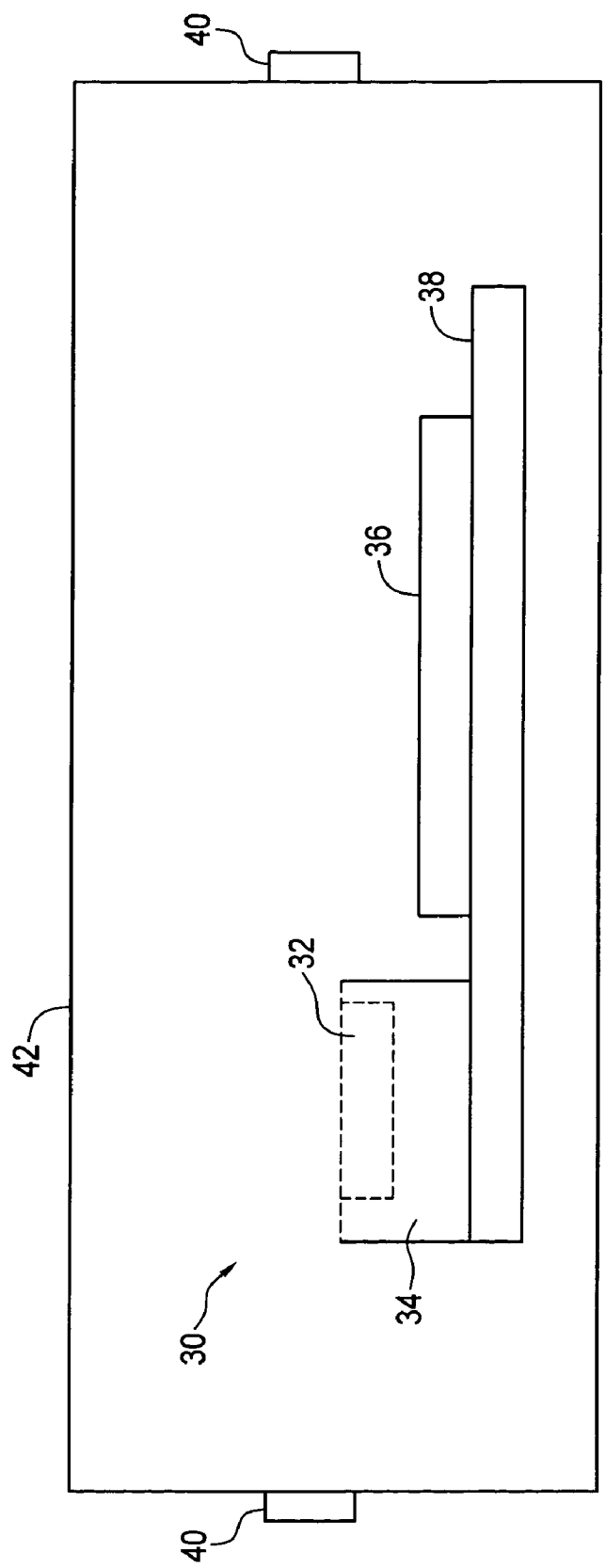
FIG. 3 illustrates a preferred embodiment peroxide sensor array system of the invention.

An example sensor array system 30 based upon the transistor 20 of FIG. 2 is shown in FIG. 3, and includes a plurality of sensors of the invention. Specifically, some of the sensors include phthalocyanine regions that exhibit decreased resistance in response to peroxides and sensors having phthalocyanine regions that exhibit increased resistance in response to peroxides. The plural sensors are included on a sensor chip 32 that is mounted in a socket 34, such as by wire bonding.

The socket provides thermal and electrical interference isolation for the chip 32 from associated circuitry 36 that is mounted on a common substrate 38, such as a PCB (printed circuit board). The PCB mounting arrangement permits, for example, the sensing system including the sensor array 30 and circuitry 36 to be incorporated into a handheld device. The circuitry 36 preferably includes circuits for driving testing for chemical analytes, receiving results from the chemical sensors, storing testing information, generating displays, etc. Interconnections between the circuitry 36 and the chip are through conventional PCB connections, and the PCB can also include circuitry related to a device that the sensor array 30 is being incorporated into. Prototype 6-pack sensor arrays demonstrated the FIG. 2 packaging arrangement to be repeatable for over 10 organic transistors made of three different materials and deposited at five different conditions.

A particular method of operation of the array system 30 maintains very low baseline drift by applying a low duty cycle, less than 50% and preferably about 10% or less, gate pulse train on the gate electrode. A low frequency signal is also preferred, less than 100 Hz and preferably below about 10 Hz, to keep the transistor operation close to its DC characteristics.

In preferred embodiments, a low duty cycle analyte dose, preferably about 10% or less, is combined with a low duty cycle pulsed gating. This permits the baseline drift for low vapor pressure analytes to be reduced to a level similar to those attained for highly volatile analytes. In a preferred embodiment, the circuitry 36 (FIG. 3) also controls valves 40 to an enclosure 42 that is part of an analyte testing to control analyte pulses in addition to gate pulses.

Figure 4B:
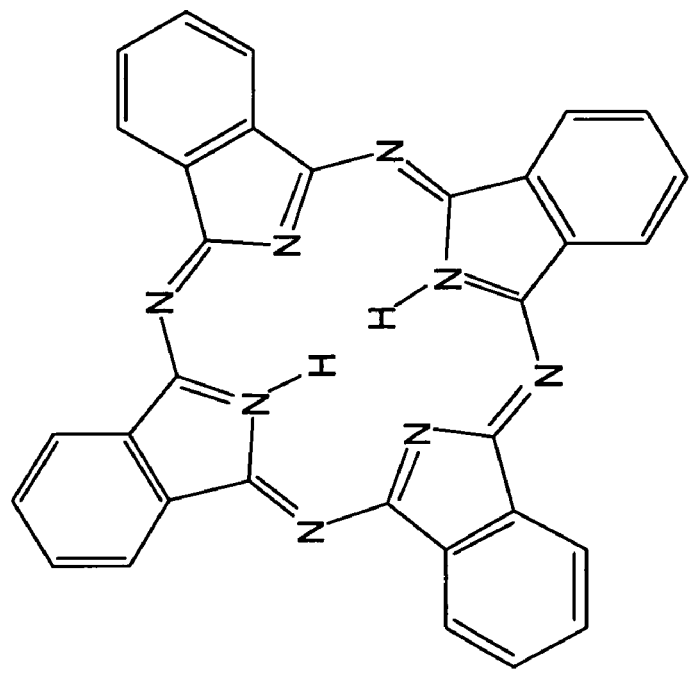
FIGS. 4A and 4B illustrate the chemical structures of example metallophthalocyanines and metal-free phthalocyanines, respectively, used in experiments of the invention.
Figure 4A:
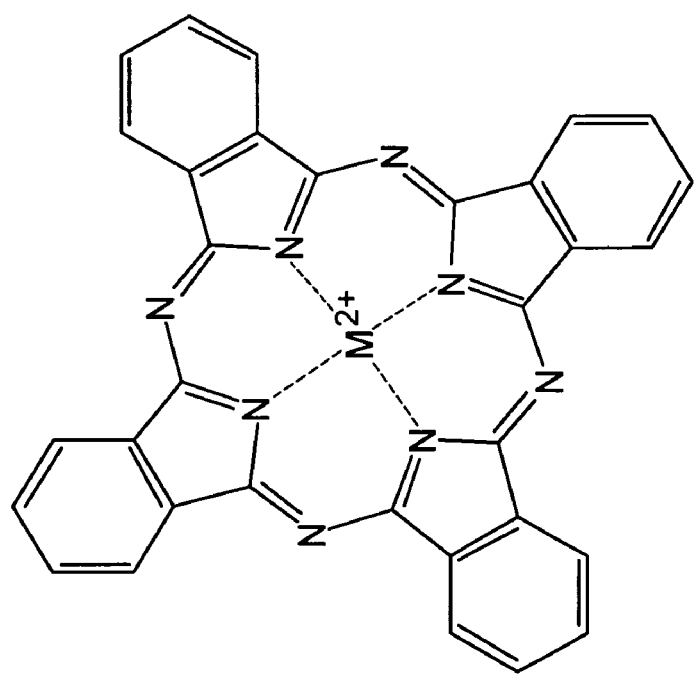

Sensing methods of the invention using sensors in accordance with FIGS. 1-3 or with other chemresistor arrangements generally make use of different phthalocyanine regions that have different peroxide reactions. FIGS. 4A and 4B illustrate the structure of metallophthalocyanines and metal-free phthalocyanines, which are macrocyclic molecules that can be used in preferred embodiments. Metallophthalocyanines may have various metal centers and organic ring substituents that allow for the tuning of selectivity. Metallophthalocyanines are exceptionally stable molecules. In vacuum they sublime with high purity at approximately 450° C., and are thermally stable up to 900° C. They are stable in the presence of strong acids and bases as well as oxidizers, and are used in preferred embodiments to take advantage of these favorable properties.

Experimental Data

Example devices consistent with the FIG. 1 embodiment were fabricated and tested. The description of the experiments will reveal additional details of preferred embodiments while artisans will also appreciate broader aspects of the invention from the experimental data.

The experiments used four different metallophthalocyanines: iron (FePc), cobalt (CoPc), copper (CuPc), and metal-free ($H_2Pc$). These molecules have good reactivity to peroxides. FePc and CoPc are known to catalyze the oxidation of hydrogen peroxide in solution and have accessible higher metal oxidation states ($Fe^{3+}$, $Co^{3+}$) CuPc has no accessible higher metal oxidation state but is widely used as a vapor sensor for other oxidizing gases such as ozone and $NO_2$ via oxidation of the phthalocyanines ring. $H_2Pc$ is generally considered to show poor sensing due to the lack of a metal center to catalyze peroxide decomposition. The peroxides analyzed in experiments included 30% $H_2O_2$ in water and di-tert-butyl peroxide as a simulant for TATP.

Electrical contacts were made to the phthalocyanine sensor films via wirebonding, providing stable, low-noise contacts. The sensors were held in a controlled environment at constant temperature in the absence of light to remove photoconductivity. Analytes were detected by measuring the film current as a function of time at a constant voltage.

A preferred dosing method was used during the experiments. The dosing method introduces analyte vapors into the sensor chamber by a system of impingers and mass flow controllers. A constant flow rate of 500 sccm (standard $cm^3$ per minute) of zero grade air was applied during the dosing/purging cycle. Analytes were introduced into the flow by impingers immersed in a Haake F8 constant temperature bath. Mass flow controllers (MKS Instruments, Inc. 1479A, 10 sccm and 1000 sccm) were used in conjunction with the impingers and a four-way valve to saturate the carrier gas with a known concentration of analyte before introduction into the sensor chamber. Solenoid valves were placed before and after each bubbler to prevent cross contamination of analytes. A Labview VI program was used to control all instruments and record data.

Electrode Fabrication

In accordance with the structure shown in FIG. 1, interdigitated electrodes were prepared by standard photolithography and lift-off processing on thermally grown $SiO_2$ (thickness of 1 μm) on (100) Si substrates. The electrodes consisted of 45 pairs of gold fingers, spaced 5 μm apart, with an electrode width of 2 mm. An adhesion layer of 5 nm Ti was applied first, followed by 45 nm of Au for a total electrode thickness of 50 nm. Six pairs of electrodes were grown on each substrate to verify sensor reproducibility and increase yield.

Thin Film Deposition

FePc (Aldrich, 90%), CuPc (Aldrich, 97%), CoPc (Aldrich, 97%), and $H_2Pc$ (Aldrich, 98%) were purified via multiple zone sublimations at 400° C. and $10^{-5}$ Torr. Films of a thickness of 50 nm were deposited on six interdigitated electrodes per substrate by organic molecular beam epitaxy in a UHV chamber with a base pressure of $2 \times 10^{-10}$ Torr. The deposition rate of the phthalocyanine films ranged from 0.2 to 0.5 Å/sec, and the deposition pressure was $5 \times 10^{-9}$ Torr. Film growth rate and thickness were monitored with a quartz crystal microbalance (QCM). The interdigitated electrodes were mounted on a temperature-controlled stage monitored with two thermocouples. Substrate temperature during deposition was held constant at 25+/−1° C. After deposition, the devices were stored under vacuum at 10 mTorr or less until use. The thickness of the films was confirmed by low angle XRD measurements performed on a Rigaku RU-200B diffractometer using Cu Kα radiation.

Analyte Preparation

The analytes used in the experiments were 30% $H_2O_2$ in water and di-tert-butyl peroxide. $H_2O_2$ (Fisher) was used as purchased, with a fresh solution for every dosing run. Di-tert-butyl peroxide (Aldrich, 98%) was used as purchased. It was kept at 2-6° C. under inert gas. Dosing concentrations for $H_2O_2$ were calculated from published techniques. $H_2O_2$ was dosed at 15, 30, 45, 60, and 75 ppm. These doses included water vapor at concentrations of 1651, 3302, 4953, 6604, and 8255 ppm, respectively. Dosing concentrations for di-tent-butyl peroxide were calculated from reported values using the known Clausius-Clapeyron equation. Di-tert-butyl peroxide was dosed at concentrations of 150, 225, 300, 375, and 450 ppm.

Results and Data

A preferred method of measuring resistance change was used in the experiments and involves continuous sensor current measurement as a function of time at constant voltage.

The responses of four different phthalocyanines (FePc, CuPc, CoPc, and $H_2Pc$) were tested with respect to two different peroxides: 30% $H_2O_2$ in water and di-tert-butyl peroxide. Phthalocyanine sensor responses are known to exhibit first order kinetics behavior and therefore have linear responses with respect to dosing concentration. It is thus unnecessary to wait for the sensor to reach saturation in response to a dose. Instead, a specific predetermined time interval can be used for each dose (in this case 5 min, but can be as fast as 1 min) gives an accurate and reproducible relative sensor response and has the added benefit of reducing response and recovery times.

Figure 5A:
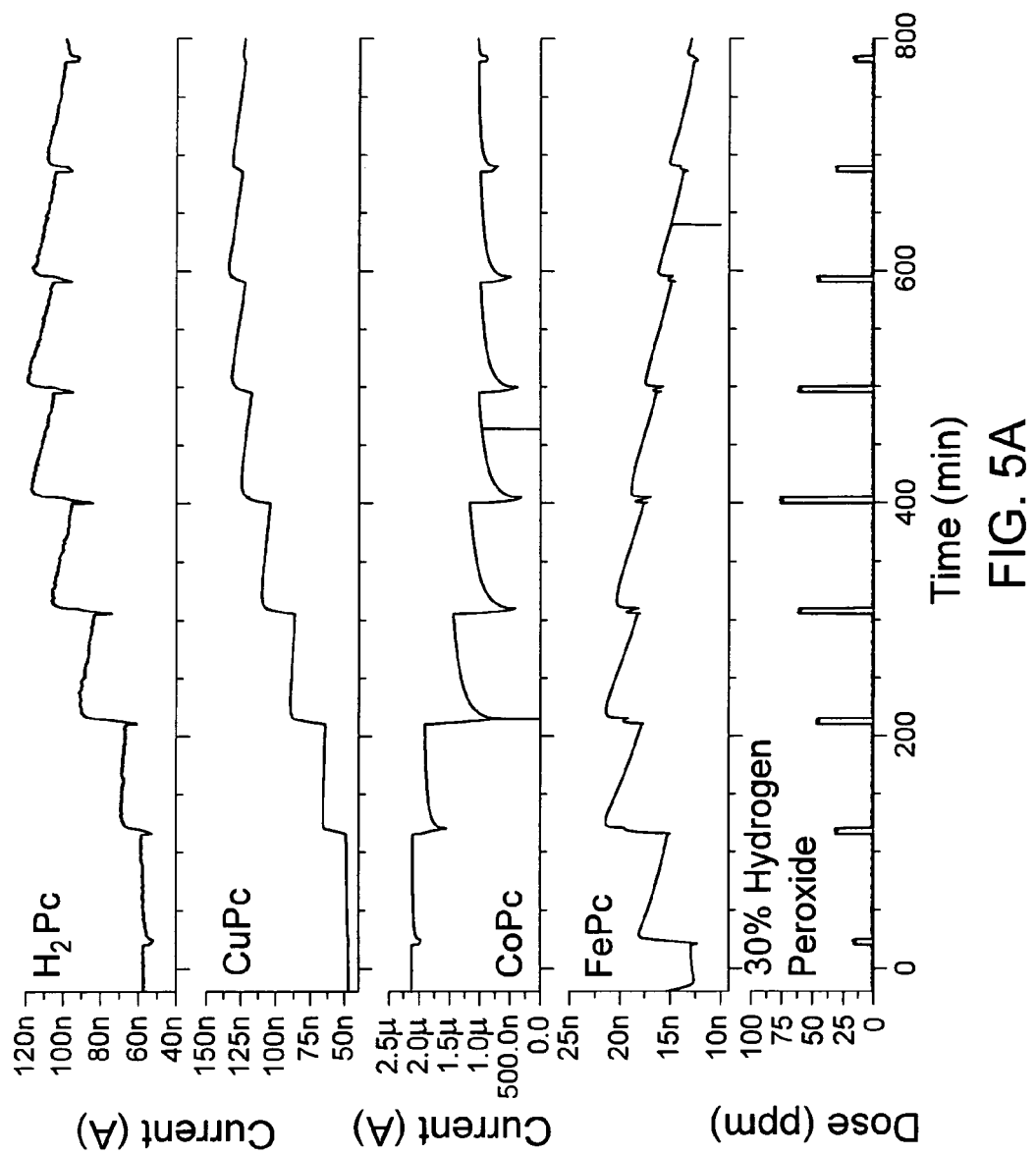
FIGS. 5A and 5B illustrate responses of experimental embodiment sensors of the invention to dosing of hydrogen and di-tert-butyl peroxide in the kinetic regime.
Figure 5B:
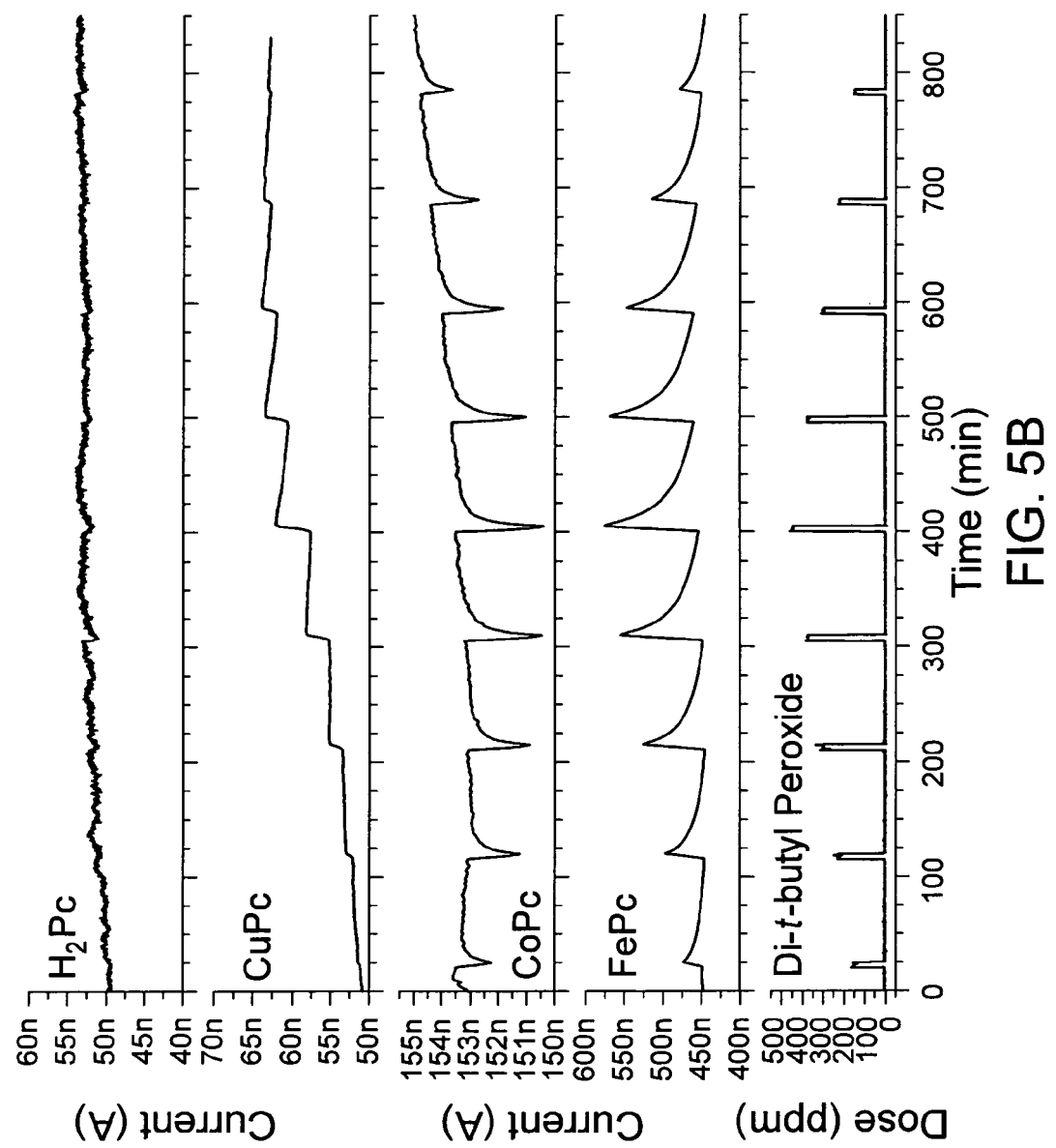
Figure 6A:
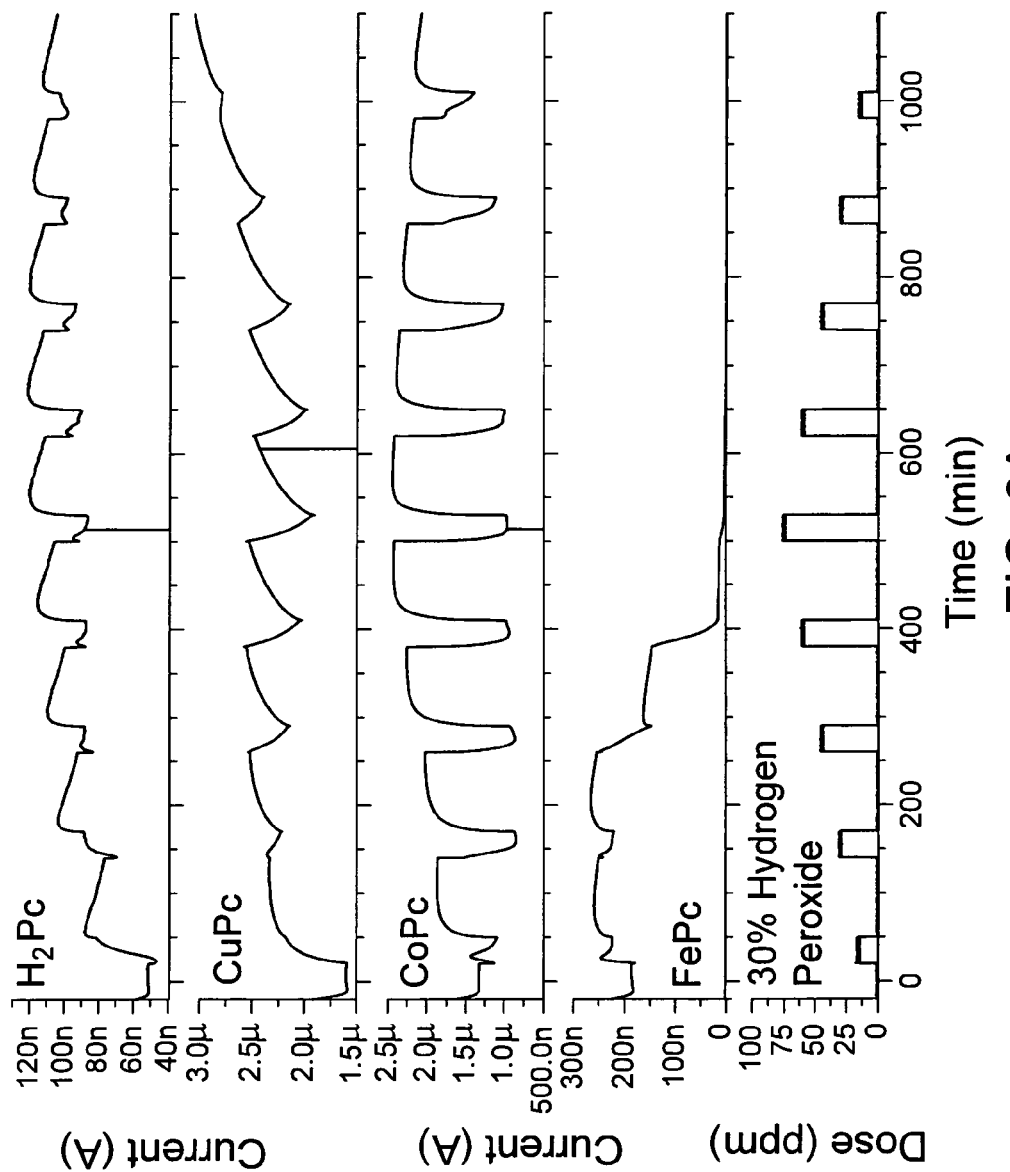
FIGS. 6A and 6B illustrate responses of experimental embodiment sensors of the invention to dosing of hydrogen and di-tert-butyl peroxide in the saturation regime.
Figure 6B:
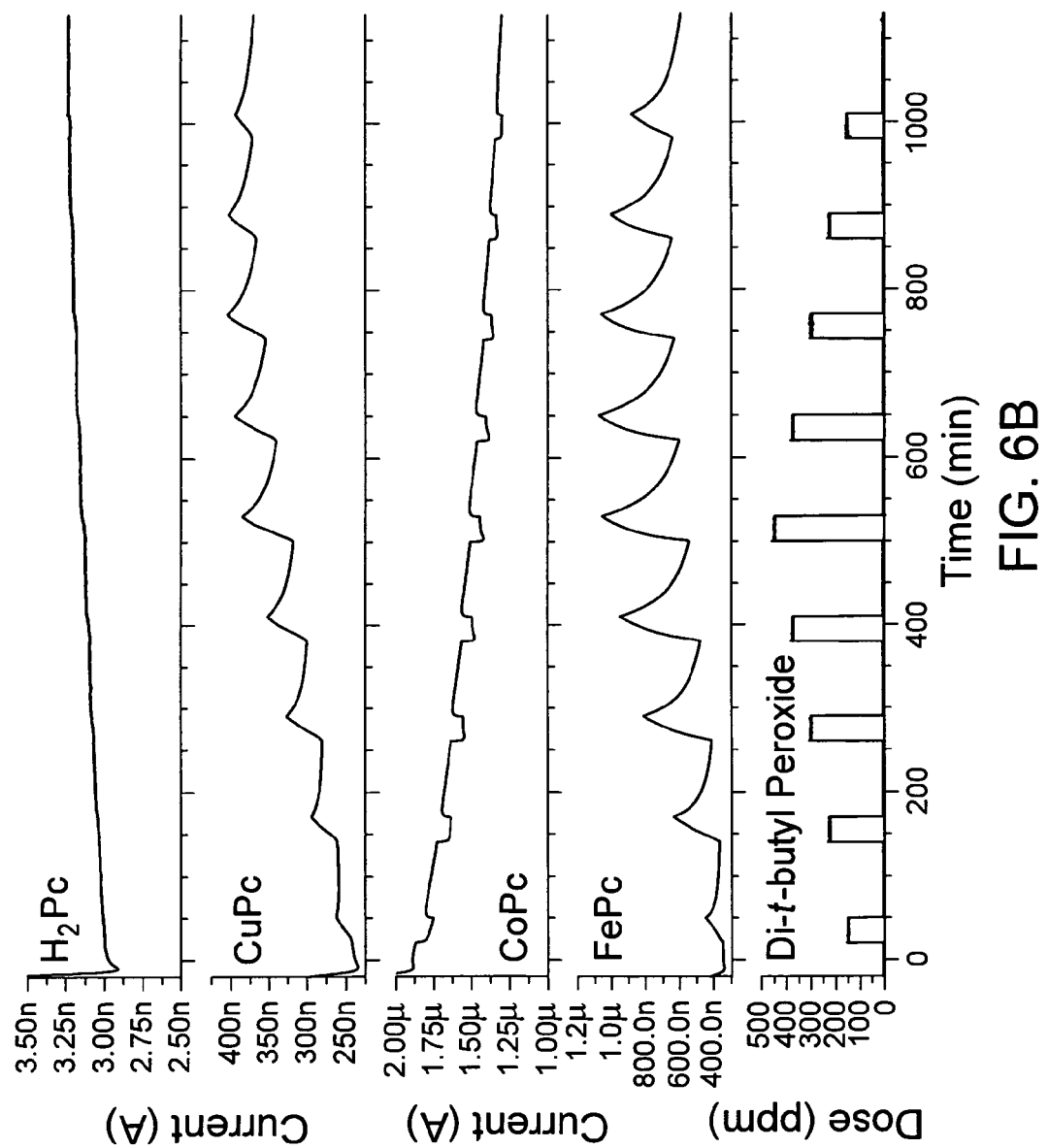

Responses of the FePc, CuPc, CoPc and $H_2Pc$ sensors were determined from the time-dependent current plots of the films when dosed with analyte. $H_2O_2$ and di-tert-butyl peroxide were dosed in the kinetic regime with a 5% duty cycle (5 min dose with a 90 min recovery) and in the saturation regime with a 25% duty cycle (30 min dose with a 90 min recovery). Water was dosed as a control for comparison to the aqueous hydrogen peroxide with a 20% duty cycle (5 min dose with a 20 min recovery). Sensing data of all MPcs to both peroxides in the kinetic regime can be seen in FIGS. 5A and 5B. Sensing data of all phthalocyanines to both peroxides in the saturation regime is shown in FIGS. 6A and 6B.

FIGS. 5A-6B qualitatively exhibit a variance in sensor reactivity with exposure to both analytes. When dosed with $H_2O_2$ the $H_2Pc$ and CuPc films are oxidized, increasing sensor current significantly. However, the currents in FePc and CoPc films are strongly reduced by $H_2O_2$. This divergence in reactivity can be attributed to the ability of $H_2O_2$ to be both oxidized and reduced on the surface of different phthalocyanines. When the sensors are dosed with di-tert-butyl peroxide different behavior is seen. CuPc films are again oxidized by the peroxide, and CoPc films exhibit minimal current decreases, suggesting physisorption interactions. FePc appears to be strongly oxidized by di-tert-butyl peroxide, while $H_2Pc$ exhibits no discernible response.

Figure 7:
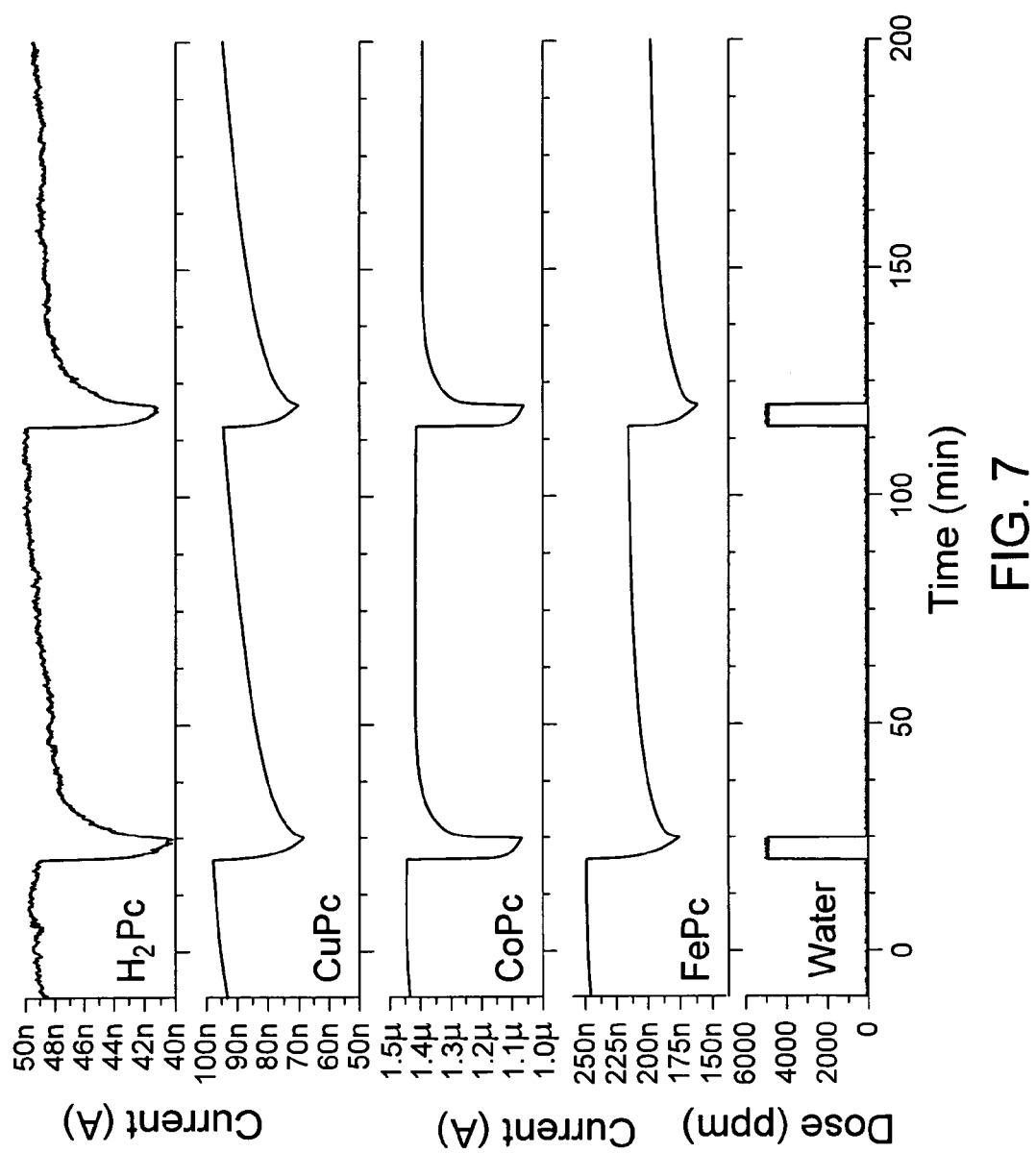
FIG. 7 illustrates responses of experimental embodiment sensors to water.

To isolate the response of the sensors to aqueous hydrogen peroxide the films dosed with an equivalent humidity of pure water vapor was also measured and the results are shown in FIG. 7. All four sensors exhibit modest current drops when exposed to water vapor, indicating that the major sensor effect is derived from $H_2O_2$, even at concentrations 2 orders of magnitude less than water. Differential analysis of the varied responses of FePc, CoPc, CuPc, and $H_2Pc$ can be used to identify peroxides from a complex background of interferents.

It can be seen qualitatively in FIGS. 5 and 6 that the changes in current of the films scale with analyte concentration. In order to quantitatively analyze the sensor responses, the percent current change was calculated for each dose, using equation [1]:

$$\% \text{ current change} = [(I_f - I_0)/I_0] * 100 \quad [1]$$

where $I_0$ is the current at the start of the dose and $I_f$ is the current at the end of the 5 min dose. This value is designated as the sensor response. Negative responses indicate current decreases, while positive responses indicate current increases. Sensor responses to analyte doses can be seen in Table 1. Phthalocyanine sensor responses for di-tent-butyl peroxide are linear with respect to analyte concentration (in general $R^2 \geq 0.97$), confirming first order analyte-film interaction kinetics. For hydrogen peroxide, however, sensor response is not linear at higher analyte concentration, suggesting a more complex mechanism of chemical sensing, likely from catalytic decomposition of the peroxide.

The redox properties of phthalocyanines have been thoroughly studied in the scientific literature. The responses of particular phthalocyanines to peroxides can be rationalized by the electronic structures of the phthalocyanines themselves. Phthalocyanines-peroxide interactions have been studied experimentally using electrochemistry (voltammetry), spectroscopy (IR, EPR, UV-Vis), and mass spectrometry. It has been reported that reductions and oxidations of $H_2O_2$ by CoPc occur at the metal center; $(Co^{III}Pc)^+$ and $(Co^{I}Pc)^-$ ions have been experimentally detected. A similar mechanism has been identified for FePc, an even more potent catalyst for $H_2O_2$ decomposition. In contrast, oxidations and reductions of CuPc have been identified as occurring on the ligand. This is also the case for $H_2Pc$, which also has no metal center to oxidize.

Results

The experiments illustrate that sensors of the invention can detected hydrogen peroxide and organic peroxide vapors in ppm amounts by interaction with nanoscale chemiresistive films of phthalocyanines. The results show that other peroxide-based explosives such as TATP can also be detected based upon the same mechanism. Analyte detection may be achieved by use of a variety of phthalocyanines, typically metal-free ($H_2Pc$), copper (CuPc), cobalt (CoPc), and iron (FePc) phthalocyanines; this list can also include MPcs with similar electronic structures, e.g., NiPc and ZnPc. Sensor responses (time dependent current at constant voltages) are seen immediately (<15 sec) upon exposure of the films to peroxide vapors. Steady state responses are seen within 20 min. Differential response analysis is used to identify the peroxide of interest. Upon exposure to $H_2O_2$, $H_2Pc$ and CuPc show current increases, while CoPc and FePc show marked current decreases. Upon exposure to di-tert-butyl peroxide $H_2Pc$ evinces minimal response, while CuPc and FePc show current increases and CoPc displays a minor current decrease. The mechanism of sensing depends on the chemical reaction of the peroxide with the phthalocyanine molecules.

The combination of two sensors with opposite current responses to specific analytes present an inexpensive and simple means to detect low ppm levels of hazardous peroxides and peroxide-based explosives. While many oxidants, such as ozone, nitrogen oxides, and halogens are known to cause an increase in conductivity (increased current or decreased resistance) of MPc sensors, peroxides are unique by virtue of the ability of some MPcs (e.g. CoPc and FePc) to catalyze oxidation of peroxides, resulting in reduction of the film and a decrease in current. Therefore, in an example dual sensor array of the invention consisting of CuPc and CoPc, an increase in current in both sensors indicates the presence of an oxidizing vapor, while a decrease in current in both sensors indicates the presence of an electron donor ligand. However, if the current in the CuPc sensor increases, while the CoPc sensor current decreases, it uniquely identifies the presence of hydrogen peroxide.

Experimental results are summarized in Table 1:

TABLE 1

Responses of sensors to the two peroxides. Units are percent current change. Negative responses denote current decreases, while positive responses denote current increases.

| Analyte | FePc Sensitivity | CoPc Sensitivity | CuPc Sensitivity | $H_2Pc$ Sensitivity |
|---|---|---|---|---|
| 30% Hydrogen Peroxide (45 ppm) | −99.9% +/− 0.1% | −55.3% +/− 2.9% | 29.4% +/− 8.9% | 54.1% +/− 8.4% |
| Water (4950 ppm) | −31.2% +/− 1.4% | −24.1% +/− 1.8% | −21.1% +/− 7.0% | −10.5% +/− 1.0% |
| Di-tert-Butyl Peroxide (450 ppm) | 82.9% +/− 11.1% | −4.7% +/− 1.1% | 18.9% +/− 1.7% | 0 |

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for sensing peroxides, the method comprising steps of:
exposing an analyte vapor to thin films of at least two phthalocyanines, one of which exhibits an oxidation reaction with peroxides and the other of which exhibits a surface or catalytic reduction reaction with peroxides;
measuring the resistance of the at least two phthalocyanines; and
determining that the analyte vapor is a peroxide when the resistance of one of the at least two phthalocyanines increases and the resistance of the other of the at least two phthalocyanines decreases.

2. The method of claim 1, wherein said step of exposing comprises introducing the analyte vapor in pulsed doses.

3. The method of claim 1, wherein said step of exposing is conducted for approximately 1 minute.

4. The method of claim 1, wherein said step of exposing is conducted for approximately 5 minutes.

5. The method of claim 1, wherein said step of measuring is conducted after conducting said step of exposing for at least 1 minute.

6. The method of claim 1, wherein the at least two phthalocyanines are selected from the group consisting of metal phthalocyanines, metal-free phthalocyanines, and chemically modified phthalocyanines.

7. The method of claim 1, wherein the at least two phthalocyanines are selected from the group consisting of copper phthalocyanine (CuPc), $CuC_{32}N_8H_{16}$, cobalt phthalocyanine (CoPc), $CoC_{32}N_8H_{16}$, metal-free phthalocyanine ($H_2Pc$), $C_{32}N_8H_{18}$, and Copper-Hexadecafluorophthalocyanine ($F_{16}CuPc$)($F_{16}CuC_{32}N_8H_{16}$).

8. The method of claim 1, wherein the thin films are ~10-100 nm) thick.

9. The method of claim 1, wherein the thin films are ultra-thin films consisting of one or a few monolayers.

10. A peroxide sensor, comprising:
thin films of at least two phthalocyanines, one of which exhibits an oxidation reaction with peroxides and the other of which exhibits a reduction reaction with peroxides; and
electrodes configured to measure the resistance of said thin films of at least two phthalocyanines.

11. The sensor of claim 10, wherein said electrodes comprise interdigitated electrode fingers and said thin films of at least two phthalocyanines are deposited upon separate sets of said interdigitated electrode fingers.

12. The sensor of claim 11, wherein thin films of at least two phthalocyanines are ~10-100 nm thick.

13. The sensor of claim 10, wherein said electrodes comprise gate electrodes isolated from drain and source electrodes by gate dielectric and said thin films of at least two phthalocyanines are arranged with respect to said gate, source and drain electrodes to act as a conduction channel in response to appropriate gate, source and drain potentials.

14. The sensor of claim 13, wherein thin films of at least two phthalocyanines are ultra-thin films consisting of one or a few monolayers.

15. A sensor system comprising:
a sensor chip having a plurality of sensors of claim 10;
a socket that mounts the sensor chip to a substrate and provides thermal and electrical interference isolation for the sensor chip; and
sensing circuitry mounted on the substrate for controlling sensing operations conducted by the plurality of sensors.

* * * * *

UNITED STATES PATENT AND TRADEMARK OFFICE
CERTIFICATE OF CORRECTION

PATENT NO. : 8,178,357 B2
APPLICATION NO. : 12/668953
DATED : May 15, 2012
INVENTOR(S) : William C. Trogler et al.

Page 1 of 2

It is certified that error appears in the above-identified patent and that said Letters Patent is hereby corrected as shown below:

| | |
|---|---|
| Title Page 2, Item [56] Col. 2, Line 35 | Please delete "at," and insert --al.,-- therefor. |
| Title Page 2, Item [56] Col. 2, Line 37 | Please delete "et. al," and insert --et. al.,-- therefor. |
| Title Page 2, Item [56] Col. 2, Line 40 | Please delete "Surf" and insert --*Surf.*-- therefor. |
| Title Page 2, Item [56] Col. 2, Line 45 | Please delete "Matenais" and insert --Materials-- therefor. |

Col. 1, Line 15    Please delete

"This invention was made with government support under AFOSR Contract No. F49620-02-1-0288 and NSF Contract No. CHE-0350571. The government has certain rights in the invention." and insert --This invention was made with government support under F49620-02-1-0288 awarded by Air Force Office of Scientific Research and under CHE-0350571 awarded by National Science Foundation. The government has certain rights in the invention.-- therefor.

| | |
|---|---|
| Col. 3, Line 53 | Please delete "Sesning" and insert --Sensing-- therefor. |
| Col. 4, Line 7 | Please delete "tert" and insert --*tert*-- therefor. |
| Col. 4, Line 9 | Please delete "tert" and insert --*tert*-- therefor. |
| Col. 4, Line 11 | Please delete "tert" and insert --*tert*-- therefor. |
| Col. 4, Line 14 | Please delete "tert" and insert --*tert*-- therefor. |
| Col. 5, Line 11 | Please delete "tent" and insert --*tert*-- therefor. |
| Col. 5, Line 29 | After "pulsed", please delete the ",". |
| Col. 8, Line 52 | Please delete "tert" and insert --*tert*-- therefor. |
| Col. 8, Line 53 | Please delete "tert" and insert --*tert*-- therefor. |
| Col. 8, Line 55 | Please delete "2-6° C" and insert --2-6 °C-- therefor. |

Signed and Sealed this
Twenty-sixth Day of February, 2013

Teresa Stanek Rea
*Acting Director of the United States Patent and Trademark Office*

CERTIFICATE OF CORRECTION (continued)
U.S. Pat. No. 8,178,357 B2

| | |
|---|---|
| Col. 8, Line 59 | Please delete "tent" and insert --*tert*-- therefor. |
| Col. 8, Line 61 | Please delete "tert" and insert --*tert*-- therefor. |
| Col. 9, Line 3 | Please delete "tert" and insert --*tert*-- therefor. |
| Col. 9, Line 15 | Please delete "tert" and insert --*tert*-- therefor. |
| Col. 9, Line 33 | Please delete "tert" and insert --*tert*-- therefor. |
| Col. 9, Line 37 | Please delete "tert" and insert --*tert*-- therefor. |
| Col. 9, Line 64 | Please delete "tent" and insert --*tert*-- therefor. |